United States Patent [19]

Likhite

[11] Patent Number: 4,816,253

[45] Date of Patent: Mar. 28, 1989

[54] **NOVEL MUTANT STRAIN OF *LISTERIA MONOCYTOGENES* AND ITS USE IN PRODUCTION OF IGM ANTIBODIES AND AS AN IMMUNOTHERAPEUTIC AGENT**

[76] Inventor: Vilas V. Likhite, 229 White St., Belmont, Mass. 02178

[21] Appl. No.: 807,170

[22] Filed: Dec. 10, 1985

Related U.S. Application Data

[60] Division of Ser. No. 519,735, Aug. 2, 1983, Pat. No. 4,567,041, which is a continuation-in-part of Ser. No. 292,193, Aug. 12, 1981, abandoned, which is a division of Ser. No. 93,171, Nov. 13, 1979, Pat. No. 4,285,930, which is a continuation of Ser. No. 858,847, Dec. 8, 1977, abandoned.

[51] Int. Cl.$^4$ .................. H61K 39/02; C12N 1/20
[52] U.S. Cl. .................. 424/92; 435/252.1; 424/93
[58] Field of Search .................. 435/253; 424/92, 88, 424/93

[56] References Cited

U.S. PATENT DOCUMENTS 3,766,162  10/1973  Spector et al. .................. 424/85
3,809,782  5/1974  Spector .................. 424/85

*Primary Examiner*—Blondel Hazel
*Attorney, Agent, or Firm*—Herbert L. Gatewood

[57] ABSTRACT

A novel mutant strain of *Listeria monocytogenes*, termed by me "*Listeria monocytogenes akka*", has been discovered which functions as a killed strain not only as an antigen resulting in the production of relatively large titers of IgM antibodies in host animals but also as an immunopotentiating agent when conjugated to a sensitising antigen, for example, living tumor cells and herpes simplex virus. The high molecular weight IgM antibodies are readily separated from serum and recovered without loss of appreciable activity. The IgM antibodies can be divided into five subunits of IgG antibodies, of lesser molecular weight, having the same specificity as the IgM immunoglobulins. When the sensitizing antigens conjugated with the *Listeria monocytogenes* strain of this invention are tumor cells, the conjugate acts as an immunotherapeutic agent effective in cancer immunotherapy.

2 Claims, No Drawings

NOVEL MUTANT STRAIN OF LISTERIA MONOCYTOGENES AND ITS USE IN PRODUCTION OF IGM ANTIBODIES AND AS AN IMMUNOTHERAPEUTIC AGENT

CROSS REFERENCE TO RELATED APPLICATIONS

This is a division of application Ser. No. 519,735, filed Aug. 2, 1983, now U.S. Pat. No. 4,567,041, which is a continuation-in-part of application Ser. No. 292,193, filed by Applicant on Aug. 12, 1981, which is a division of application Ser. No. 93,171, filed Nov. 13, 1979, now U.S. Pat. No. 4,285,930, which issued Aug. 25, 1981, which is a continuation of Application Serial No. 858,847, filed December 8, 1977, now abandoned.

BACKGROUND OF THE INVENTION (1) Field of the Invention

This invention relates to a novel mutant strain of *Listeria monocytogenes*, to its use in the production of high titers of IgM antibodies specific thereto, to its use and functioning as an immunopotentiating agent (or immunostimulant adjuvant) when conjugated to a sensitizing antigen, to the antibodies responsive to the mutant strain or conjugate, and to such conjugates used as immunotherapeutic agents for use in the treatment of various diseases.

(2) Description of the Prior Art

Immunity is an everyday word applied to a special category of defenses possessed by the body, i.e., the reticuloendothelial and lymphoproliferation systems, by means of which infectious agents, e.g., antigens, may be checked or destroyed even after they have entered the body tissues. The immunity is largely due to the development within the body of substances known as antibodies (or immune bodies) which interact specifically with the antigen destroying or inactivating the disease causing agent. Immunity may be natural or acquired, and in the latter case may be acquired naturally or artificially. Artificial immunity, as is well known, can be either passive, i.e., by injection of an antiserum (prophylactic, therapeutic), or active, as by vaccination with, for example, live or dead organisms.

Antigens, which may either be introduced into or formed in the body, generally speaking, may be defined as those physiological substances such as proteins, animal products, bacteria, viruses, hormones, chemical vitamins, lipopolysaccharides, peptides, etc., which, when injected into an animal system, human or not, stimulate the production of a specific protein mechanism, i.e., the antibody response, which enables the animal injected to defend or react against that antigen. A further, more detailed, description of antigens is set forth in P. L. Carpenter, *Immunology and Serology,* (2d Edition, 1968); however, typical antigens may be classified as follows:

(1) protein antigens, such as ceruloplasmin and serum albumin;
(2) bacterial antigens, such as teickoic acids, flagellar antigens, capsular polysaccharides, and extra-cellular bacterial products and toxins;
(3) blood group antigens, such as glycoproteins and glycolipids;
(4) viruses, such as animal, plant, and bacterial viruses;

(5) conjugated and synthetic antigens, such as proteinhapten conjugates, and synthetic polypeptides; and
(6) nucleic acides, such as ribonucleic acid and deoxyribonucleic acid.

By the term antibody is meant broadly any substance which is mutually attracted to the antigen and which can be observed to combine with and have a neutralizing effect on the antigen. Antibodies, from a somewhat more specific definition, are those physiological agents which, in an animal system, stimulate the production of a serum protein called immunoglobulins (or sometimes "gamma globulins") for defending against the antigen encountered. The immunoglobulins (Ig) are actually a family of closely related, though not identical, proteins, of which there are five major types, IgG, IgA, IgD, IgE, and IgM, varying in molecular weight from approximately 160,000 to approximately 1,000.000. The IgG (or immunoglobulin gamma G) type is the most prevalent "antibody" in a serum and is characterized by a molecular weight of about 160,000. The IgM type is the least prevalent and is characterized by a molecular weight of about 1,000,000.

Although the antigen-antibody reaction forms the basis for immunity, that is the state of being immune to or protected from disease, especially an infectious disease, the reaction also is the basis for the whole field of immunochemistry which field includes not only immunization but also diagnostic medicine and immnuotherapy.

Immunization procedures are important in the prevention of various diseases including viral diseases. Sometimes it is necessary that a large supply of antibodies appear in a person's blood immediately in order to combat an overwhelming infection already present in the body. Accordingly, the patient must receive ready-made antibodies, and various commercial means of manufacture and recovery of various antibodies have been developed over the years.

In more recent years, there has grown an ever increasing need for commercial sources of antibodies for use in various immunoassays, both radioimmunoassays and, even more recently, enzymeimmunoassays. Such assays are used for various purposes, e.g., determination of pregnancy, detecting the presence of heroin and other opiate alkaloids in a person's physiological fluids, e.g., urine, and detection of hepatitis.

There has also developed considerable evidence that viruses cause various kinds of tumors and cancerous growths, particularly in lower animals such as rabbits, mice, chickens, and hamsters. Various investigators, including the present Applicant, have also been active in their attempt to discover agents that might be effective in cancer immunotherapy. See Likhite, V. V., "Clinical Cancer Immunotherapy: Experience in Breast and Lung Cancer", in *Immunocancerology in Solid Tumors,* (Martin, M. and Dionne, L., eds.) pp. 135–141. (Stratton, 1976). "Rejection of Tumor Metastases in Fisher 344 Rats Following Administration of Killed *Corynebacterium parvum*", *Cancer Immunology and Immunotherapy,* (1977), Vol. 2, pp. 173–178 V. V. Likhite. Thus, with this and other interests in immunotherapy there is a continuing and growing need for antibodies.

Basically, there are two methods for the isolation and purification of antibodies. One method involves separation of groups of molecules based upon their physical properties such as molecular weight. Inherent in this approach is the fact that similar molecules regardless of immunological specificity will be isolated together. The second method of isolation of antibodies involves immunological methods which depend upon a primary characteristic of all antibodies, i.e., their ability to react with specific antigens. Thus, if an antigen is added to a serum containing a specific antibody, the antigen and antibody will complex and precipitate from the solution:

Antigen+Antibody=Antigen-Antibody Complex

Once separated from the solution the antigen can be removed from the complex by dissociation followed by physical separation if the two molecules are sufficiently different. The basic difficulty with the above separation technique is that, in general, complete separation of antigen from antibody is not achieved. As a result, there is always some residual antigen left in any antibody recovered, making for an antibody preparation of less than the desired specificity.

Campbell et al., Proc. Nat'l. Acad. Sci. (U.S.) 37,575 (1951) discovered that antibodies could be isolated and purified which did not contain residual antigen by covalently coupling antigens to insoluble polymers before reacting with antibody in a serum sample. Since these earlier studies on immuno-adsorbents, several types of polymers have been employed as carriers for antigens. These include cellulose and its derivatives, polyaminopolystyrene, dextrose, and polyaminoacids. Generally, these materials have been found satisfactory; however, each has certain specific drawbacks. Some of the problems with these materials involve (a) release of nonspecific protein adsorbed onto the carrier earlier from serum with release of the antibody; (b) decreasing flowrates from the immunoadsorbent column; (c) immunoadsorbent efficiency, i.e., the percentage of antibody retained on the immunoadsorbent in relation to the total antibody added; (d) the period of usefulness of the particular immunoadsorbent and yield, due to irreversible complexing resulting in fewer sites available for reuse; and (e) loss of biological activity. As a result, the search has continued over the years, and still continues, for improved methods for isolating and purifying antibodies.

Examples of this continuing search are the inventions disclosed in U.S. Pat. Nos. 3,652,761 and 3,843,444. In the former patent, either antigens or antibodies are disclosed to be stabilized by chemical coupling to an inorganic carrier by means of an intermediate silane coupling agent rather than being merely adsorbed onto a carrier. These immunochemical composites, according to the patentee, are biologically active, have acceptable capacity, excellent antigen-antibody association-dissociation characteristics, and can be reused over and over many times. Nevertheless, the fact remains that this procedure of isolation of antibodies from antigens is attendant with some of the very same problems as earlier procedures where, e.g., an antigen was insolubilized on an immunoadsorbent. This results from the mutual attraction that antibodies and antigens have for one another.

The approach disclosed in U.S. Pat. No. 3,843,444, which issued to the Applicant herein on Oct. 22, 1974, for separating biological substances such as antibodies and antigens from a liquid is to make use of the mutual attraction that such substances have for one another. However, the antibodies and antigens are prevented from actually contacting one another by the interdisposition of a thin semipermeable membrane, to the opposite sides of which the antibodies and antigens are attracted. The antibodies are then subsequently washed from the membrane surface by hypertonic saline at 37° C., after the membrane surface is first washed with physiological saline, to wash away the non-antibody protein attracted to the surface. Thus, a rather high percentage of the available antibody is recovered in a rather simple process and with substantially unimpaired physiological properties.

Nevertheless, even with ever improving methods of isolation and purification of antibodies, the fact remains that the availability of antibodies for immunization, diagnostic or therapeutic purposes is still limited due to the limit of conferred antibody response in the host. Moreover, when an animal receives repeated injections of a given antigen, the induced specific antibody response in the host animal against the injected antigen represents a relatively small amount, usually less than 1% of the serum globulin pool.

Thus, there is still a need not only for a method of producing larger quantities of antibodies within a biological system, but also improved methods of recovering antibodies from serum and without appreciable loss of activity.

Heretofore others have disclosed the adjuvant effect with the combined immunization with two or more antigens in a single injection. Each antigen is reinforced and simultaneously produces immunity. Moreover, Meacock et al., Chemical Abstracts, 79 64410X (1973) Effect of adjuvant and stress in the production of IgE antibody in rats, disclose the enhanced production of IgE antibody in rats through injection of Bordetella pertussis cells within twenty-four hours before or after the injection of antigen. Likhite, V. V., "Clinical Cancer Immunotherapy: Experience in Breast and Lung Cancer", Immunocancerology in Solid Tumors, supra, discloses that killed Corynebacterium parvum had been discovered by others earlier not only to be effective as an immunostimulant adjuvant but also to have immunotherapeutic properties toward neoplasms. Thus, Likhite, as disclosed in that publication, investigated further the possible immunotherapeutic effects of B. pertussis, widely confirmed to have immunopotentiating properties, toward cancer. The results revealed that only the group of animals treated with a cancer cell (e.g., T1699)—B. pertussis conjugate survived. The conjugate was formed by coupling the tumor cells at 4° C. to toluene,-2,4-diisocyanate followed by coupling the killed B. pertussis microorganism to the 2d carbon position at 37° C.

Numerous other investigators have been active in recent years in their attempt to discover agents that might be effective in cancer immunotherapy. British Pat. No. 1,193,378 discloses a therapeutic agent which comprises water-soluble cancer antigens such as human tumor or leukemia antigen coupled to foreign proteins such as gamma globulins used to vaccinate human patients against cancer. When such an antigen complex is used, as disclosed in that patent, the therapeutic effect is to retard or at least slow down the progress of the disease involved in the patient. The patentee hypothesized that the entire complex acts as an antigen causing the patient to manufacture antibodies in his blood against the vaccine complex and each of its components, soluble human cancer antigens as well as the foreign protein portion of the complex. According to the patentee anti-human tumor and anti-rabbit gamma globulin antibodies may be demonstrated in the vaccinated patient's sera by titering their sera against the vaccine complex and each of its components (soluble human cancer antigen and soluble rabbit gamma globulin). The antibodies thus developed, the patent discloses, apparently attack the cancer antigens in the patient such as tumor antigens and the tumor itself and cause the rate of growth to slow down or even cease.

SUMMARY OF THE INVENTION

Now, in accordance with the basic aspects of the invention, there has been discovered a novel mutant strain of Listeria *monocytogenes* which has as one of its strain characteristics, when killed and injected into a host animal, utility as an antigen in causing the production of larger titers of IgM antibodies specific thereto than heretofor possible.

A subculture of the newly discovered bacteria strain *Listeria monocytogenes akka* has been deposited with, and can be obtained upon request, from the permanent collection of the Northern Regional Research Laboratories (NRRL), Agricultural Research Services, U.S. Department of Agriculture, Peoria, Ill., U.S.A. Its accession number in this repository is NRRL B-11,233.

The IgM antibodies produced in accordance with the invention are readily and easily recovered from serum, and further purified without loss of appreciable activity. Thus, as the antibodies recovered retain their antigen-specific immunochemical characteristics, they will be found quite useful not only in diagnostic medicine and analytical biochemistry but also, therapeutic immunology.

Quite advantageously, the IgM antibodies produced in accordance with the invention being pentamers of IgG antibodies can, subsequent to recovery, be divided into subunits of IgG antibodies by means of physiologically mild reducing agents, and without appreciable loss of their specific activity. Thus, there is provided a ready source for even larger quantities of antibodies, as needed.

A further, and most important, characteristic of the *Listeria monocytogenes* mutant strain disclosed herein is its immunopotentiating properties when conjugated with a sensitizing antigen. Thus, when injected into an animal, high titer antibody response is induced specific to the antigen conjugate.

When the sensitizing antigen is a physiological substance such as a bacteria, virus, tumor cells, or other infectious agent, the conjugate, quite advantageously, will be found useful as an immunotherapeutic agent.

The specific IgM antibodies of the invention, or the subunits thereof, e.g. IgG antibodies, can be, moreover, quite advantageously, tagged or labeled with a vital dye (stain) for use in diagnostic applications. This permits use of conventional light microscopy instead of fluorescent microscopy. Also, if desired, the antibodies can be tagged with various radioisotopes or enzymes, according to usual techniques, for use in radio-or enzyme-immunoassay.

IgM antibodies according to the invention can be, moreover, coupled with chemotherapeutic agents such as antibodies and anticancer drugs, e.g. organic pharmaceuticals, for the treatment of the specific disease-causing agents (towards which the antibody has already been formed). Thus, in accordance with a further aspect of the invention, there can be provided a chemotherapeutic product effective in the treatment of, e.g. pathogenic bacteria or tumors, or viral infections.

DETAILED DESCRIPTION OF THE INVENTION AND THE PREFERRED EMBODIMENTS THEREOF

The novel mutant strain Listeria monocytogenes akka of this invention provides not only a means of producing larger quantities of antibodies in a host animal but, most importantly, a means of recovering those antibodies as pure and active antigen-specific-antibodies. This results from the fact that the *Listeria monocytogenes akka* mutant strain induces a response to IgM antibodies, and such antibodies are characterized by their insolubility in cold temperature, e.g. 4° C., making for ease in separation and recovery of a purified product, from the serum, as hereinafter more fully disclosed. The IgM antibodies go back into solution when suspended in physiological buffer solution with heating to 31° C.

As the IgM antibodies maintain their antigen specific immunochemical characteristics, they are more desirable for use in diagnostic and therapeutic immunology. The purified antibody, i.e., the antibody recovered, reacts only with the Listeria monocytogenes akka organism or the coupled antigen and organism, according to the invention.

The IgM antibodies can, if desired, be separated into five subunits of IgG antibodies, which also exhibit the same specificities as the IgM antibodies, by exposure to various mild physiological reducing agents. Examples of these are mercaptoethanol and cysteine. Thus, it is possible to produce higher titers than heretofore of IgG antibodies, and of a desirable purity, which can be used in various immunochemical applications.

Although the recovery of the IgM antibodies is most desirably based on their insolubility at cold temperatures, this method of recovery need not be the only one employed. Sheep red blood cells can be used, according to conventional techniques. Other methods of recovery of IgM antibodies include column chromatography using Sephadex or Sepharose 6200, the IgM antibodies being represented in the first peak of protein eluted. These alternative methods are less preferred, however, as they do result in some, though not appreciable, loss of specific activity.

It has also been discovered, quite unexpectedly, that a protein extract from the culture medium in which the microorganisms of the invention are grown induces the same antibody response as the microorganism. After the *Listeria monocytogenes akka* is recovered, the culture medium is saturated with $(NH_4)_2SO_4$, and allowed to precipitate out overnight. It is then dialized against standard buffer and used the same as if it were the microorganism recovered.

Quite advantageously, the *Listeria monocytogenes akka* mutant strain of the invention functions as an immunopotentiating agent, or as such might also be called, an immunopostimulant adjuvant, when chemically coupled to a sensitizing antigen. When injected into an animal, this antigen conjugate induces the production of relatively high titers of IgM antibody, in some cases reaching quantities as high as 6 gm percent in the host serum, an unexpectedly high response.

The sensitizing antigen can be any of those commonly known as antigens; however, it desirably will be a physiological substance toward which specific antibodies are desired. Thus, the sensitizing antigen can be an infectious substance such as viral agents, e.g., Herpes simplex virus, malaria parasite, bacteria, e.g., staphylococcus aureus bacteria, diphtheria toxoid, tetanus toxoid, shistosomula, tumor cells, e.g. CAD2 mammary adenocarcinomia tumor cells, and hormones such as thyroxine $T_4$, triiiodothyronine $T_3$, and cortisol. IgM antibodies recovered from a host animal as a response to injections of such antigen conjugates will be found to react specifically and only with the *Listeria monocytogenes*, the particular sensitizing antigen, and the conjugate. Thus, when *Listeria monocytogenes akka* is conjugated to live tumor cells, it will, when injected into an animal having such a tumor, including a human being, function as an immunotherapeutic agent, inducing a response that results in rejection of the tumor. Or when an antigen conjugate, for example, couples a virus with the immunopotentiating agent, the injection of such a conjugate into an animal affects treatment of the viral infection by stimulation of host defenses against that viral infection.

The coupling of the sensitizing antigen to the immunopotentiating agent, i.e., the *Listeria monocytogenes akka* mutant strain can be accomplished by means of various chemical agents having two reactive sites such as, for example, bisdiazobenzidine, glutaraldehyde, diiodoacetate, and diisocyanates, e.g., m-xylenediisocyanate and toluene-2,4-diisocyanate. The latter coupling agent is more preferred for a number of reasons. First of all the NCO groups readily react with free $NH_2$ groups. However, and this is a most desirable feature in using toluene-2,4 diisocyanate, only the NCO group at the 4th carbon remains active at 4° C. Thus, its use as a coupling agent permits coupling of the killed bacteria strain first at the 4th carbon position, followed by coupling of the sensitizing antigen at the second carbon position. If desired, however, the so-called "sensitizing antigen" can be coupled to the 4th carbon position first, followed by coupling of the immunopotentiating agent to the 2nd carbon position. Thus, it will be appreciated that a conjugate formed in this two-step fashion will provide an antigen conjugate molecule with predetermined spatial order, making for more specific antibody response than where the *Listeria monocytogenes akka* and sensitising antigen are randomly coupled together.

It will be appreciated also that the sensitizing antigen need not necessarily have $-NH_2$ groups for the coupling with toluene-2,4-diisocyanate (TDIC). Any sensitizing antigen will be found satisfactory in the practice of the invention, provided $-NH_2$ groups can be added to it, if necessary. Obviously TDIC need not be the only coupling agent used, to provide the desired controlled order coupling. Any other coupling agent can be used, in the preferred practice of the invention, which will permit two step manufacture of the antigen conjugate.

The preparation of antibodies is a well established practice and is believed to require no detailed explanation herein. Immunization can be carried out in a variety of ways with a number of different animals. Although rabbits have been used in the practice of the invention, other animals, e.g. mice, rats, goats and sheep can be substituted as hosts. Any mammal capable of immune response can be employed as the host animal in antibody production. For the most part for commerical production of antibodies, relatively large animals are employed, such as equine, bovine, porcine, canine, ovine, caprine, rodentia, rabbits and hares.

The antigenic material may be injected interperitoneally, intramuscularly, subcutaneously and the like. When employing Freund's adjuvants, usually in combination with saline, the amount of antigen employed will vary depending on the particular antigenic material and the number and period of prior injections. Usually, about 0.1 to 5 mg of antigenic material will be employed per one ml of solution. The total amount of antigenic material and emulsion will depend on the size, nature and weight of the animal employed. The initial injection will normally be at a number of sites, aliquots of the composition being employed.

The first injections of antigen conjugate serve to load the animal, and a period of time is allowed to pass before booster injections are introduced, normally from 1 to 5 weeks. Bleeding may occur after each injection, if desired, so as to follow the formation of the desired antibody. Depending on the animal, bleedings can be carried out via heart puncture, the carotid artery or external jugular vein. After recovery from the serum, hereinafter more fully disclosed, the IgM antibodies will normally be stored at reduced temperature, pending further use. Numerous preservatives are known which can be employed, if desired, to stabilize the antibodies.

The invention may be more fully understood by reference to the following examples which illustrate certain embodiments of the invention.

EXAMPLE 1

Preparation of Killed Mutant Strain of Listeria Monocytogenes akka

Using conventional sterile technique a novel strain of *Listeria monocytogenes* (*Listeria monocytogenes akka*) was isolated from a patient having lung cancer but who died from listeriosis. The isolate was grown in 500 ml standard culture medium (Todd-Hewitt), according to known procedures, over a period of about 24 hours.

The culture medium was then heated at 60° C. for a sufficient time, e.g. about one hour, to kill the bacteria. This was determined by lack of growth when the material was placed on blood agar plates.

The broth was next centrifuged according to conventional techniques at 3000 g for 20 minutes to harvest the killed bacteria cells, the supernate being saved for extraction of the associated active protein.

The recovered killed bacteria cells were then suspended in 50 ml standard Phosphate Buffered Saline (PBS, pH 7.4) and this suspension then centrifuged, as previously described, and the bacteria cells again harvested. The procedure was then twice repeated to make certain the cells were clean. The *Listeria monocytogenes akka* cells were then ready for use, in accordance with the invention, in the manufacture of IgM antibodies or preparation of an antigen compound or conjugate as desired.

EXAMPLE 2

Production of IgM Antibodies Using Killed Mutant Strain of *Listeria Monocytogenes akka*

The harvested, killed *Listeria monocytogenes akka* cells from Example 1 were again suspended in standard PBS, pH 7.4, and then were, according to usual technique, injected into experimental animals over a period of several weeks.

When the animals were bled and antibody titer determined, it was found to be unexpectedly high. The IgM antibodies recovered were found to be antigen-specific to the novel mutant strain of *Listeria monocytogenes akka*.

EXAMPLE 3

Production of Antigen Conjugate with Bovine Serum Albumin

Killed *Listeria monocytogenes akka* cells, as in Example 1, were resuspended in 6 ml standard PBS, pH 8.6, in a 25 ml Ehrlenmeyer flask, and the contents placed at 4° C. for 30 minutes. Toluene-2,4-diisocyanate (TDIC), which meanwhile had been cooled to 4° C., was then added dropwise to the flask, with constant stirring, over a period of 1 hour, 100 mg total being added. This solution was then allowed to sit for 30 minutes so that the TDIC was coupled with the killed bacteria cells.

The suspension was then centrifuged (3000 g for 20 minutes) and the supernatant material discarded. The recovered antigen compound (*Listeria monocytogenes akka*-TDIC) was then resuspended in 8 ml std. PBS, pH 7.4, and again washed by centrifugation, as before, to remove any uncoupled bacteria cells.

The washed antigen compound was then resuspended in 6 ml std. PBS, pH 7.4, and 500 mg bovine serum albumin (50% solution in std. PBS, pH 7.4, dialyzed previously according to conventional techniques) was then added to the suspension. This mixture was then placed at 37° C. and stirred (magnetic stirrer) for 1 hour, after which it was allowed to sit for 30 minutes. The suspension was then washed by centrifugation, as before described. It was then determined according to usual techniques that 2 mg bovine serum (BSA) were conjugated to $10^9$ bacterial cells. The antigen conjugate thus prepared was then stored at $-70°$ C. until ready for use.

EXAMPLE 4

Production of IgM Antibody Responsive to Antigen Conjugate 0.25 ml of a solution of the *Listeria monocytogenes akka*-TDIC-BSA conjugate (std. PBS, pH 7.4, according to usual technique) produced in the previous example were injected intravenously into each of several experimental rabbits at weekly intervals for five weeks, during which time the rabbits were producing IgM antibodies in response to the presented antigen conjugate.

A week following the last injection, the rabbits were bled (from 50 ml to 120 ml of blood was obtained from each rabbit). The antibody titer was determined according to conventional procedures and was found to be unexpectedly high. Measurements were discontinued because of the high titer after 1/6,000,000 dilution of the serum.

At this point, the blood can either be allowed to heparinize or clot (at 37° C.) for further processing.

EXAMPLE 5

Recovery of IgM Antibodies Specific to *Listeria Monocytogenes-Akka*Tdic-Bsa Antigen Conjugate The blood samples from the rabbits of Example 4 were allowed to clot and the serum then placed at 4° C. for 24 hours. At this temperature the gamma M globulins (due to their inherent nature) precipitate and can then be recovered. This was accomplished by centrifugation (1000 g × 10 min.) at 4° C., after which the precipitated IgM antibodies were washed twice by centrifugation, using cold std. PBS, pH 7.4.

The recovered precipitate was then resuspended in std. PBS, pH 7.4, depending on the original volume of blood, and these suspensions warmed to room temperature, at which time the precipitate became soluble.

In this manner from 2 to 7 grams of gamma M globulins were separated. 6 mg of the globulins recovered reflected about 1/250,000 titer to BSA, indicating that all antibody recovered was albumin specific.

EXAMPLE 6

SUBDIVIDING IgM ANTIBODIES INTO SUBUNITS OF IgG ANTIBODIES

An equal volume of the IgM antibodies from Example 5 was added to 0.06M cysteine in std. PBS, pH 7.4 and this mixture was incubated at 37° C. for two hours. This caused the gamma M globulins to separate into gamma G globulin subunits. These antibodies are found to react in the same manner with the albumin as the IgM antibodies without loss of specific activity.

EXAMPLE 7

PRODUCTION OF ANTIBODY RESPONSIVE TO ANTIGEN CONJUGATE HAVING AS SENSITIZING ANTIGEN THYROXINE ($T_4$) HORMONE, STAPHYLOCOCCUS AUREUS BACTERIA OR HERPES SIMPLEX I VIRUS

Using sterile technique, a loopful of *Listeria monocytogenes akka* bacteria were innoculated in a culture flask with one liter (1000 ml) of commercially available sterile Brain & Heart Infusion (BHI) nutrient broth. The innoculate was then incubated at 37° C. in a standard laboratory incubator for 36 hours.

The bacteria were then killed by placing the culture flask on a standard laboratory hot plate at 100° C. for 30 minutes. The broth was then allowed to cool to room temperature, after which the broth was centrifuged in sterile 100 ml centrifuge tubes (screw top) at 2000 rpm for 15 minutes.

The supernatant of the media was discarded and the killed bacteria recovered were washed twice by adding sterile saline to the bacteria, resuspending them and centrifuging at 2000 rpm for 15 minutes. The killed *Listeria monocytogenes akka* cells were then pooled together in a sterile 250 ml flask using 150 ml of sterile phosphate buffered saline, pH 7.5.

About 100 ml of the PBS containing the killed bacteria was placed in a sterile flask to which 15 mg of toluene-2,4-diisocyanate in 10 ml PBS was added, at 4° C. The mixture formed was then stirred with a magnetic stirrer for two hours, while held at 4° C. Then about 25 ml of the mixture was placed in each of four 50 ml conventional screw top tubes and centrifuged at 2000 rpm for 15 minutes. The supernatant was discarded and the antigen compound recovered (*Listeria monocytogenes akka*-TDIC) was washed with 25 ml cold PBS (4° C.) twice by centrifugation (2000 rpm × 15 min.). After the second wash, the recovered antigen compound was suspended in PBS (pH 7.0).

To each suspension was then added one of the following in 10 ml of cold PBS (pH 7.0): (1) 20 mg Bovine Serum Albumin (BSA); (2) 10 mg Thyroxine $T_4$; (3) freshly killed staphylococcus aureus bacteria; and (4) lyophilized Herpes simplex virus. The resultant mixtures were then placed at 37° C. and stirred for 2 hours in an incubator. Afterwards, the mixtures were each transferred to separate sterile 50 ml screw top tubes and washed with PBS by centrifuging at 2000 rpm, three times, at fifteen minutes each. Each conjugate recovered was then resuspended in PBS (pH 7.0).

Forty-eight New Zealand white rabbits (approximately 1.2 to 2 kg) were divided into eight groups of six animals each. Each animal in each group was then given (according to conventional techniques), weekly injections (0.5 ml) for six weeks of one of the following: (1) BSA admixed with Freund's adjuvant (injected subcutaneously); (2) *Listeria monocytogenes akka*-TDIC-BSA (injected intravenously); (3) Thyroxine $T_4$ (100 mg) admixed with Freund's adjuvant (subcutaneously); (4) *Listeria monocytogenes akka*-TDIC-Thyroxine $T_4$ (approx. 50 mg, intravenously); (5) staphylococcus aureus bacteria ($50 \times 10^8$, killed, admixed with Freund's adjuvant, subcutaneously); (6) *Listeria monocytogenes akka*-TDIC-S. Aureus ($5 \times 10^9$ bacteria, intravenously); (7) Herpes simplex virus (admixed with Freund's adjuvant, subcutaneously); and (8) *Listeria monocytogenes akka*-TDIC-Herpes simplex virus (intravenously).

Six weeks after the last injection the rabbits were bled using standard laboratory procedures. About 30–50 cc of blood was obtained from each animal and was placed in sterile heparinized tubes and kept at 37° C. The blood was then centrifuged at 37° C. (2000 rpm × 15 min.) The supernatant plasma was separated from the red cells using sterile Pasteur pipettes and then placed in sterile 50 ml test tubes, after which an equal quantity of PBS (pH 7.4) was added to the plasma in each tube. About 1 ml of the solution from each tube was then separated for antibody screening.

The remaining solution was placed at 4° C. for 24 hours. Each tube was then centrifuged at 4° C. (2000 rpm × 15 min.) and the supernatant separated from each tube. Only the tubes from the *Listeria monocytogenes akka* antigen conjugate injected had a precipitate. This was resuspended in equal volumes of PBS (pH 7.4) at 37° C. Although the tubes which contained the serum from rabbits injected with Freund's adjuvant mixtures did not have a precipitate, the tubes nevertheless also each received PBS (pH 7.4, 37° C.), after centrifuging.

Each tube was then placed at room temperature and 1 ml of the liquid was separated and tested for antibody activity. The results are summarized in the table below.

ANTIBODY ACTIVITY

| Rabbit No. | Immunizing Procedure | Initial Titer Plasma | Plasma Precipitate Present at 4° C. | Post 4° C. Precipitate Solution Titer |
|---|---|---|---|---|
| 1 | Bovine Serum | 1:1000 | 0 | 0 |
| 2 | Albumin mixed | 1:500 | 0 | 0 |
| 3 | with Freund's | 1:2000 | 0 | 0 |
| 4 | adjuvant[1] | 1:2500 | 0 | 0 |
| 5 | injected | 1:1500 | 0 | 0 |
| 6 | subcutaneously | 1:250 | 0 | 0 |
| 7 | *Listeria-mono-* | 1:1.5 million | + | 1:7.0 million |
| 8 | *cytogenes* akka- | 1:5.0 million | + | 1:12 million |
| 9 | TDIC-Bovine | 1:7.0 million | + | 1:10 million |
| 10 | Serum Albumin | 1:2 million | + | 1:5 million |
| 11 | injected | 1:800,000 | + | 1:3 million |
| 12 | intravenously | 1:3 million | + | 1:7 million |
| 13 | Thyroxine | 1:2000 | 0 | 0 |
| 14 | ($T_4$)[2] admixed | 1:5000 | 0 | 0 |
| 15 | with Fruend's | 1:2500 | 0 | 0 |
| 16 | adjuvant | 1:7500 | 0 | 0 |
| 17 | injected | 1:6000 | 0 | 0 |
| 18 | subcutaneously | 1:4000 | 0 | 0 |
| 19 | Thyroxine | 1:7.0 million | + | 1:12 million |
| 20 | ($T_4$)-TDIC- | 1:2.5 million | + | 1:6 million |
| 21 | *Listeria mono-* | 1:3.5 million | + | 1:5 million |
| 22 | *cytogenes akka* | 1:3.2 million | + | 1:6 million |
| 23 | injected in- | 1:3.4 million | + | 1:7 million |
| 24 | travenously | 1:7.0 million | + | 1:11 million |

-continued

ANTIBODY ACTIVITY

| Rabbit No. | Immunizing Procedure | Initial Titer Plasma | Plasma Precipitate Present at 4° C. | Post 4° C. Precipitate Solution Titer |
|---|---|---|---|---|
| 25 | *Staphylococcus* | 1:500 | 0 | 0 |
| 26 | *aureus* | 1:2000 | 0 | 0 |
| 27 | (killed) | 1:2500 | 0 | 0 |
| 28 | admixed with | 1:1000 | 0 | 0 |
| 29 | Freund's | 1:4000 | 0 | 0 |
| 30 | adjuvant injected subcutaneously | 1:6000 | 0 | 0 |
| 31 | *Listeria* | 1:500,000 | + | 1:2 million |
| 32 | *monocytogenes* | 1:2.0 million | + | 1:6 million |
| 33 | akka-TDIC- | 1:800,000 | + | 1:2 million |
| 34 | *Staphylococcus* | 1:1.5 million | + | 1:2.5 million |
| 35 | *aureus* | 1:3.0 million | + | 1:4.0 million |
| 36 | injected intravenously | 1:1.2 million | + | 1:2 million |
| 37 | Herpes simplex | 1:500 | 0 | 0 |
| 38 | virus ad- | 1:250 | 0 | 0 |
| 39 | mixed with | 1:1000 | 0 | 0 |
| 40 | Freund's | 1:500 | 0 | 0 |
| 41 | adjuvant | 1:250 | 0 | 0 |
| 42 | injected subcutaneously | 1:50 | 0 | 0 |
| 43 | *Listeria* | 1:800,000 | + | 1:2 million |
| 44 | *monocytogenes-* | 1:1.0 million | + | 1:2 million |
| 45 | TDIC-Herpes | 1:250,000 | + | 1:1 million |
| 46 | simplex virus | 1:250,000 | + | 1:800,000 |
| 47 | injected | 1:1.0 million | + | 1:2 million |
| 48 | intravenously | 1:1.5 million | + | 1:2.5 million |

[1]Complete Freund's adjuvant
[2]Tested against thyroid bound globulin TB6
0 = absence of precipitate;
+ = precipitate present

EXAMPLE 8

PRODUCTION OF ANTIBODY RESPONSIVE TO *LISTERIA MONOCYTOGENES AKKA*-TDIC-BSA CONJUGATE

This example further illustrates the process, according to the invention, of producing and purifying antibody to Bovine Serum Albumin (BSA) when used as the sensitizing antigen and conjugated with *Listeria monocytogenes akka.*

*Listeria monocytogenes akka* bacteria were cultivated in sterile Brain-Heart-Infusion (BHI) nutrient broth obtained commercially. A loopful of bacteria, using sterile technique, was innoculated in a culture flask containing about 1000 ml of the liquid media. The culture media was then incubated in a standard incubator at 37° C. for 36 hours.

The bacteria were then killed by placing the flask on a standard laboratory hot plate at 100° C. for 30 minutes. When the temperature of the flask (which was removed from the hot plate) reached room temperature, the culture media containing the killed bacteria was placed in sterile 100 cc centrifuge tubes and centrifuged (using a standard centrifuge) at 2000 rpm for 15 minutes. The supernatant media was discarded and the bacteria were washed (twice) by placing sterile saline in the centrifuge tubes and then again centrifugating at 2000 rpm for 15 minutes. The killed bacteria were then pooled together in one 250 ml sterile flask using 150 ml of sterile Phosphate-Buffered-Saline (PBS) pH 7.4.

Twenty ml of the bacterial suspension was then placed in a 50 ml sterile flask to which 5 mg of toluene-2,4-diisocyanate in 5 ml of PBS had been added at 4° C., and the mixture was stirred using a magnetic stirrer for 2 hours. The mixture was then placed in 50 cc sterile screw top test tube and centrifuged at 2000 rpm for 15 minutes. The supernatant was discarded and 20 ml of sterile PBS was added and the procedure was repeated twice. Subsequently, the Listeria monocytogenes akka-TDIC compound was resuspended in Phosphate-Buffered Saline, pH 7.0.

100 mg Bovine Serum Albumin (BSA) in 10 ml of PBS pH 7.0 was then added to the suspension. The resultant mixture was then placed at 37° C. and stirred with a magnetic stirrer for 2 hours. At this time, the mixture was transferred to sterile 50 ml screwtop tubes and then centrifuged at 2000 rpm×15 minutes at room temperature. The supernatant was then discarded and 20 ml of PBS pH 7.0 was added and the previous centrifugation procedure repeated. Again the supernatant was discarded and 20 ml of PBS, pH 7.0, added and the centrifugation procedure repeated. the supernatant was again discarded and the Listeria monocytogenes akka-TDIC-BSA conjugate recovered was placed in 20 ml PBS, pH 7.4.

Twenty-four New Zealand White Rabbits (approximately 1.5 to 2 kg) were used for production of antibody. These animals, kept under standard laboratory conditions and at room temperature, were separated into four groups of 6 animals each and each animal of a group received weekly (×6) intravenous injections (PBS pH 7.4, 0.75 ml) of one of the following: (1) BSA, 1 mg; (2) BSA (1 mg) in Fruend's adjuvant (subcutaneously administered); (3) a conjugate of a routine strain of Listeria-monocytogenes-TDIC-BSA (coupled with BSA 1 mg); and (4) the conjugate produced herein of Listeria monocytogenes akka-TDIC-BSA (1 mg).

Four to six weeks after the last injection, the rabbits were bled using routine laboratory procedures (central artery of the ear) and about 30 to 60 cc of the blood was obtained from each animal and placed in sterile heparinized test tubes and kept at 37° C. The blood was then centrifuged at 37° C. (2000 rpm×15 min) and the subsequent plasma was separated from the red blood cells using sterile Pasteur pipettes and then placed in sterile 50 ml test tubes. About 1 ml of the plasma from each animal was tested for standard antibody evaluation using BSA (50 mg in 100 ml PBS pH 7.5) and standard techniques. The remaining plasma from each animal was diluted with equal volumes of PBS pH 7.4 and then placed at 4° C. for 24 hours. Each sample was then centrifuged (2000 rpm, 15 minutes) at 4° C. and the supernatant discarded. The centrifugation procedure was repeated after placing each sample in 20 ml PBS pH 4.7 (4 degrees C). The supernatant was again discarded and to each test tube 20 ml of PBS pH 7.4 (37° C.) was added and the tube placed at 37° C. for 1 hour. Then each tube was placed at room temperature and 1 ml of the solution separated for antibody testing (using the 0.5 mg BSA in PBS pH 7.4). The results, summarized in Table 1 below, revealed that only the animals immunized with the novel strain of Listeria monocytogenes akka-TDIC-BSA conjugate produced extremely high quantities of antibodies which could then be purified at 4° C. These antibodies were then identified to be rabbit IgM using standard immunological detecting techniques and goat-anti rabbit IgM antibody.

ANTIBODY ACTIVITY AGAINST BSA

| Rabbit No. | Immunizing Procedure (weekly × 6 weeks) | Initial* Titer Plasma | Precipitate at 4° C. | Post 4° C. Precipitate Solution Titer |
|---|---|---|---|---|
| 1 | Bovine Serum | 1:640 | 0 | 0 |
| 2 | Albumin | 1:640 | 0 | 0 |
| 3 | (1 mg) | 1:64 | 0 | 0 |
| 4 | alone | 1:64 | 0 | 0 |
| 5 | | 1:320 | 0 | 0 |
| 6 | | 1:256 | 0 | 0 |
| 7 | Bovine Serum | 1:2000 | 0 | 0 |
| 8 | Albumin | 1:2500 | 0 | 0 |
| 9 | (1 mg) | 1:1000 | 0 | 0 |
| 10 | in complete | 1:3200 | 0 | 0 |
| 11 | Freund's | 1:516 | 0 | 0 |
| 12 | adjuvant | 1:640 | 0 | 0 |
| 13 | (routine | 1:2500 | 0 | 0 |
| 14 | strain) | 1:3500 | 0 | 0 |
| 15 | Listeria- | 1:5000 | 0 | 0 |
| 16 | monocytogenes- | 1:10,000 | 0 | 0 |
| 17 | TDIC-Bovine | 1:2000 | 0 | 0 |
| 18 | Serum Albumin conjugates | 1:4000 | 0 | 0 |
| 19 | (novel | 1:2 million | + | 1:12 million |
| 20 | strain) | 1:5 million | + | 1:10 million |
| 21 | Listeria- | 1:7 million | + | 1:16 million |
| 22 | monocytogenes- | 1:800,000 | + | 1:7 million |
| 23 | TDIA-Bovine | 1:1.5 million | + | 1:12 million |
| 24 | Serum Albumin conjugates | 1:5 million | + | 1:20 million |

*titer: + reaction to dilution. Therefore, 1:516 means 1 to 516 dilution
0 = absent to negligible;
+ = present As many different embodiments of this invention will now have occurred to those skilled in the art, it is to be understood that the specific embodiments of the invention as presented herein are intended by way of illustration only and are not limiting on the invention, but that the limitations thereon can be determined only from the appended claims.

What I claim is:

1. A culture of the mutant strain of the microorganism Listeria monocytogenes having the identifying characteristics of NRRL B-11,223, said mutant strain when killed being useful as an antigen for the production of relatively large titers of IgM antibodies specific thereto.

2. A protein extract of the mutant strain of the microorganism Listeria Monocytogenes having the identifying characteristics of NRRL-B-11,223 according to claim 1.

* * * * *